US007822478B2

(12) United States Patent
Killian et al.

(10) Patent No.: US 7,822,478 B2
(45) Date of Patent: *Oct. 26, 2010

(54) COMPRESSED NEURAL CODING

(75) Inventors: Matthijs Killian, Mechelen (BE); Bas van Dijk, Mechelen (BE); Andreas Buechner, Isernhagen (DE); Joerg Pesch, Hannover (DE); Marc Majoral, Brussels (BE); John Parker, Roseville (AU); James Finlay Patrick, Roseville (AU); Ernst Von Wallenberg, Basel (CH)

(73) Assignee: Cochlear Limited, Lane Cove (AU)

(*) Notice: Subject to any disclaimer, the term of this patent is extended or adjusted under 35 U.S.C. 154(b) by 1006 days.

This patent is subject to a terminal disclaimer.

(21) Appl. No.: 11/094,769

(22) Filed: Mar. 31, 2005

(65) Prior Publication Data

US 2005/0192648 A1  Sep. 1, 2005

Related U.S. Application Data

(63) Continuation-in-part of application No. 10/343,397, filed as application No. PCT/AU01/01032 on Aug. 21, 2001, now Pat. No. 7,272,446.

(60) Provisional application No. 60/557,675, filed on Mar. 31, 2004, provisional application No. 60/616,216, filed on Oct. 7, 2004.

(51) Int. Cl.
A61N 1/36 (2006.01)

(52) U.S. Cl. .......................................... 607/57

(58) Field of Classification Search .................. 607/57
See application file for complete search history.

(56) References Cited

U.S. PATENT DOCUMENTS

| 4,441,202 A | 4/1984 | Tong et al. |
| 4,515,158 A * | 5/1985 | Patrick et al. .................. 607/57 |
| 4,532,930 A | 8/1985 | Crosby et al. |
| 4,611,596 A | 9/1986 | Wasserman |
| 5,046,242 A | 9/1991 | Kuzma |
| 5,274,711 A | 12/1993 | Rutledge et al. |
| 5,403,262 A | 4/1995 | Gooch |
| 5,412,748 A | 5/1995 | Furuyama et al. |
| 5,687,282 A | 11/1997 | Van De Kerkhof |
| 5,776,179 A | 7/1998 | Ren et al. |

(Continued)

FOREIGN PATENT DOCUMENTS

EP          0247649          12/1987

(Continued)

OTHER PUBLICATIONS

European Search Report, EP 01 95 9971, dated Aug. 11, 2005.

(Continued)

*Primary Examiner*—Kennedy J Schaetzle
(74) *Attorney, Agent, or Firm*—Kilpatrick Stockton LLP

(57) ABSTRACT

An embodiment of the present invention takes masking effects into consideration when determining stimulations signals for neural stimulation. These masking effects may be modeled using user-specific models determined by taking measurements for an implant system of an implant recipient. Or, the model may correspond to a group of individuals sharing a common characteristic or the population as a whole. These models may be, for example, psycho-physical or electrophysiological models.

46 Claims, 11 Drawing Sheets

U.S. PATENT DOCUMENTS

| | | | |
|---|---|---|---|
| 5,824,022 | A | 10/1998 | Zilberman et al. |
| 5,895,416 | A | 4/1999 | Barreras et al. |
| 6,198,971 | B1 | 3/2001 | Leysieffer |
| 6,230,057 | B1 | 5/2001 | Chow et al. |
| 6,321,126 | B1 | 11/2001 | Kuzma |
| 6,463,328 | B1 | 10/2002 | John |
| 6,537,200 | B2 | 3/2003 | Leysieffer et al. |
| 6,565,503 | B2 | 5/2003 | Leysieffer et al. |
| 6,575,894 | B2 | 6/2003 | Leysieffer et al. |
| 6,594,525 | B1 * | 7/2003 | Zierhofer ............... 607/57 |
| 6,697,674 | B2 | 2/2004 | Leysieffer |
| 6,751,505 | B1 | 6/2004 | Van Den Honert et al. |
| 6,778,040 | B2 | 8/2004 | Kim |
| 6,778,858 | B1 * | 8/2004 | Peeters ................. 607/57 |
| 7,272,446 | B2 * | 9/2007 | Parker et al. ............. 607/57 |
| 7,328,151 | B2 * | 2/2008 | Muesch ................ 704/228 |
| 2001/0050837 | A1 | 12/2001 | Stevenson et al. |
| 2003/0109903 | A1 | 6/2003 | Berrang et al. |
| 2003/0233133 | A1 | 12/2003 | Greenberg et al. |
| 2004/0098063 | A1 | 5/2004 | Goetz |
| 2004/0147992 | A1 | 7/2004 | Bluger et al. |

FOREIGN PATENT DOCUMENTS

| | | |
|---|---|---|
| EP | 0 282 336 A2 | 11/1988 |
| JP | 61001200 | 1/1986 |
| JP | 63242252 | 10/1988 |
| JP | 8501241 | 2/1996 |
| JP | 10508442 | 8/1998 |
| JP | 11-513539 T | 11/1999 |
| JP | 2000509566 | 7/2000 |
| WO | WO 93/24176 | 12/1993 |
| WO | WO 95/01709 | 1/1995 |
| WO | WO 96/12383 | 4/1996 |
| WO | 9709863 A1 | 3/1997 |
| WO | 97/43871 A1 | 11/1997 |
| WO | WO 97/48447 | 12/1997 |
| WO | 9965276 | 12/1999 |
| WO | 0103622 | 1/2001 |
| WO | 0119304 | 3/2001 |
| WO | 0199470 | 12/2001 |

OTHER PUBLICATIONS

International Preliminary Examination Report, PCT/AU01/01032, dated Apr. 10, 2002.

International Search Report, PCT/Au01/01032, dated Oct. 5, 2001.

Abbas, et al., "Electrically Evoked Compound Action Potentials Recorded from Subjects Who Use the Nucleus C12M Device," *Gantz et al. Seventh Symposium on Cochlear Implants in Children.*

Baumgarte, et al., "A Nonlinear Psychoacoustic Model Applied to the ISO MPEG Layer 3 Coder," *Institut für Theoretische Nachrichtentechnik und Informationsverarbeitung, Universität Hannover, Germany.*

Edler, et al., "ASAC-Analysis/Synthesis Audio Codec for Very Low Bit Rates," *Institut für Theoretische Nachrichtentechnik und Informationsverarbeitung, Universität Hannover, Germany.*

Cohen, et al., "Spatial spread of neural excitation in cochlear implant recipients: comparison of improved ECAP method and psychophysical forward masking," *Hearing Research*, 179 (2003) 72-87.

Cohen, et al., "Spatial spread of neural excitation: comparison of compound action potential and forward-masking data in cochlear implant recipients," *International Journal of Audiology 2004*: 43: 346-355.

Miller, et al., "An Improved Method of Reducing Stimulus Artifact in the Electrically Evoked Whole-Nerve Potential," *Ear & Hearing*, 2000 by Lippincott Williams & Wilkins, USA.

Bernd Edler, Heiko Purnhagen, and Charalampos Ferekidis, *ASAC—Analysis/Synthesis Audio Codec for Very Low Bit Rates*, 100th AES Convention, Copenhagen (May 1996).

Frank Baumgarte, Charalampos Ferekidis, and Hendrik Fuchs, *A Nonlinear Psychoacoustic Model Applied to the ISO MPEG Layer 3 Coder*, 99th AES Convention, New York (Oct. 1995).

Lawrence T. Cohen, Louise M. Richards, Elaine Saunders, and Robert S.C. Cowen, *Spatial Spread of Neural Excitation in Cochlear Implant Recipients: Comparison of Improved ECAP Method and Psychophysical Forward Masking*, 179 Hearing Res. 72-87 (May 2003).

Abbas PJ, Brown CJ, Hughes ML, Ganz BJ, Wolaver AA, Gervais JP and Hong SH, *Electrically evoked compound action potentials recorded from subjects who use the nucleus C124M device*, 185 Ann Otol Rhinol Laryngol Suppl. 6-9 (Dec. 2000).

Lawrence T. Cohen, Elaine Saunders, and Louise M. Richardson, *Spatial Spread of Neural Excitation: Comparison of Compound Action Potential and Forward-Masking Data In Cochlear Implant Recipients*, 43 International Journal of Audiology 346-355 (2004).

Miller CA, Abbas PJ, Brown CJ, *An Improved Method of Reducing Stimulus Artifact in the Electrically Evoked Whole Nerve Potential*, 21(4) Ear Hear 280-90 (Aug. 2000).

CA Examiner's report dated May 29, 2007.

Nogueira et al. "A Psychoacoustic 'NofM'- Type Speech Coding Strategy for Cochlear Implants,"EURASIP Journal on Applied Signal Processing, pp. 3044-3059, 2005.

Supplementary European Search Report dated Aug. 11, 2005.

First European Examiners's Report for European Application No. 01959971.1 dated dated Nov. 23, 2005.

Second CA Office Action dated Dec. 10, 2008.

Japanese Patent Application No. 2002-561453, Notice of Reasons for Rejection dated Jun. 16, 2009.

* cited by examiner

COMPRESSED NEURAL CODING

CROSS-REFERENCE TO RELATED APPLICATIONS

This is a continuation-in-part of application Ser. No. 10/343,397, filed Feb. 21, 2003, entitled "Power Efficient Electrical Stimulation," now U.S. Pat. No. 7,272,446, which is the national stage of PCT application PCT/AU01/01032, filed Aug. 21, 2001, which claims priority to Australian Patent Application No.:PQ9528 filed Aug. 21, 2000. This application also claims the benefit of the following two U.S. provisional applications. The first application is U.S. Provisional Application No. 60/557,675, entitled "Spread of Excitation and MP3 Coding," filed Mar. 31, 2004. The second is U.S. Provisional Application No. 60/616,216, entitled "Spread of Execution and Compressed Audible Speech Coding," filed Oct. 7, 2004. The entire disclosure and contents of the above applications are hereby incorporated by reference herein in their entirety.

This application also makes reference to the following U.S. Patent Applications. U.S. application Ser. No. 10/478,675, entitled "A Peak-Derived Timing Stimulation Strategy for a Multi-Channel Cochlear Implant," filed Nov. 24, 2003 now U.S. Pat. No. 7,312,558; U.S. Application No. 60/548,104, entitled "Rotable Belt Clip for Body-Worn Speech Processor," filed Feb. 27, 2004; U.S. Application No. 60/548,094, entitled "Reversible Belt Clip for Body-Worn Speech Processor," filed Feb. 27, 2004; U.S. application Ser. No. 10/798,847, entitled "Virtual Wire Assembly having Hermetic Feedthroughs," filed Mar. 12, 2004 now U.S. Pat. No. 7,174,223; U.S. Application No. 60/557,713 "Ramping Pulse Train Stimulation," filed Mar. 31, 2004. The entire disclosure and contents of the above applications are hereby incorporated by reference herein.

BACKGROUND

1. Field of the Invention

The present invention relates generally to neural stimulation and, more particularly, to taking masking effects into account when select stimulation signals for neural stimulation.

2. Related Art

Wearable medical devices reliant upon stored power share a common dynamic. As the possible and desired functionality of the devices is improved, the power demands generally also increase. As a result, the life per charge or per cell is reduced, which has not only a cost impact for the user, but also increases the risk that a device will power down at an inconvenient time.

In the field of cochlear implants, this issue is exacerbated by the trend to a single, behind the ear unit to replace what was once a head mounted unit and a separate speech processor unit worn on the body. The available volume and weight for the power cell is accordingly reduced. Increased power demands to provide improved functionality create a need to consider the efficiency of speech processing schemes and stimulus sets in order to provide maximum battery life.

SUMMARY

Methods and systems are provided of neural stimulation. These methods and systems include determining a plurality of stimulation signals based on a received signal, selecting a subset of one or more of the plurality of stimulation signals based on information indicative of a masking effect of at least one of the plurality of stimulation signals, and applying stimuli to a neural structure of a user based on the selected subset of stimulation signals.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DETAILED DESCRIPTION

Embodiments of the present invention are described below in connection with one embodiment of an exemplary implantable medical device, a cochlear™ prosthesis (also referred to as a cochlear implant system, cochlear prosthetic device and the like; "cochlear prosthesis" herein). Cochlear prostheses use direct electrical stimulation of auditory nerve cells to bypass absent or defective hair cells that normally convert acoustic vibrations into neural activity. Such devices generally use multi-contact electrodes inserted into the scala tympani of the cochlea so that the electrodes may differentially activate auditory neurons that normally encode differential pitches of sound. Such devices are also used to treat a smaller number of patients with bilateral degeneration of the auditory nerve. For such patients, a cochlear prosthetic device provides stimulation of the cochlear nucleus in the brainstem.

Figure 1:
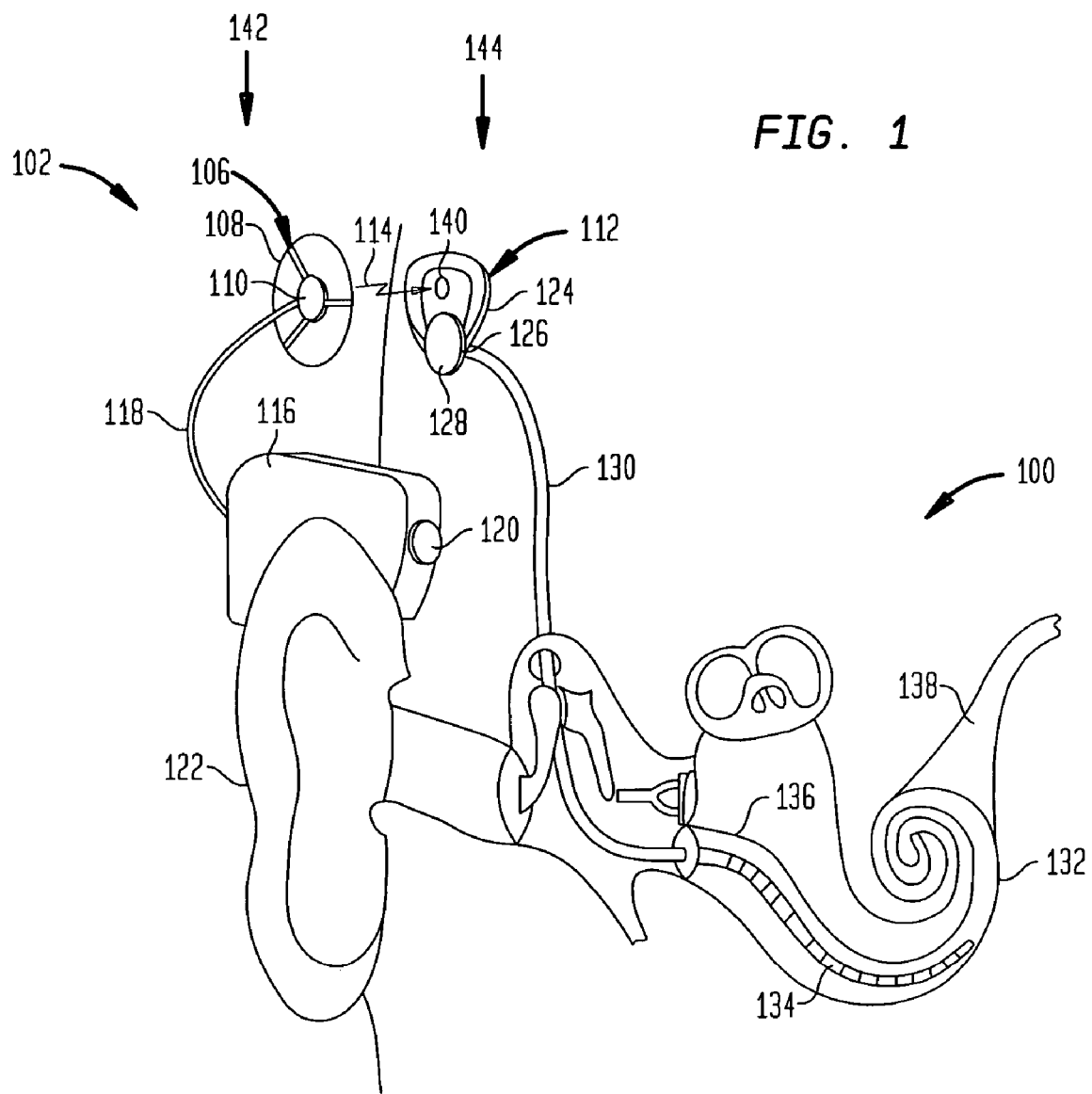
FIG. 1 is a schematic block diagram of one embodiment of an exemplary acoustic prosthesis suitable for implementing embodiments of the present invention.

Exemplary cochlear prostheses in which the present invention may be implemented include, but are not limited to, those systems described in U.S. Pat. Nos. 4,532,930, 6,537,200, 6,565,503, 6,575,894 and 6,697,674, which are hereby incorporated by reference herein. FIG. 1 is a schematic diagram of an exemplary cochlear implant system 100 in which embodiments of the present invention may be implemented. Cochlear implant system 100 comprises external component assembly 142 which is directly or indirectly attached to the body of the recipient, and an internal component assembly 144 which is temporarily or permanently implanted in the recipient. External assembly 142 typically comprises audio pickup devices 120 for detecting sound, a speech processing unit 116 a power source (not shown), and an external transmitter unit 106. External transmitter unit 106 comprises an external coil 108, and preferably, a magnet 110 secured directly or indirectly to external coil 108. Speech processing unit 116 processes the output of audio pickup devices 120 that are positioned, in the depicted embodiment, by the ear 122 of the recipient. Speech processing unit 116 generates coded signals, referred to herein as a stimulation data signals, which are provided to external transmitter unit 106 via cable 118.

Internal components 144 comprise an internal receiver unit 112, a stimulator unit 126, and an electrode array 134. Internal receiver unit 112 comprises an internal transcutaneous transfer coil 124, and preferably, a magnet 140 fixed relative to internal coil 124. Internal receiver unit 112 and stimulator unit 126 are hermetically sealed within a housing 128. Internal coil 124 receives power and data from external coil 108, as noted above. A cable 130 extends from stimulator unit 126 to cochlea 132 and terminates in electrode array 134. Signals generated by stimulator unit 126 are applied by array 134 to the basilar membrane 136, thereby stimulating the auditory nerve 138.

Collectively, transmitter antenna coil 108 (or more generally, external coil 108) and receiver antenna coil 124 (or, more generally internal coil 124) form an inductively-coupled coil system of a transcutaneous transfer apparatus 102. In one embodiment, external coil 108 transmits electrical signals to internal coil 124 via a radio frequency (RF) link 114. Internal coil 124 is typically a wire antenna coil comprised of at least one and preferably multiple turns of electrically insulated single-strand or multi-strand platinum or gold wire. The electrical insulation of internal coil 124 is provided by a flexible silicone molding (not shown). In use, implantable receiver unit 112 may be positioned in a recess of the temporal bone adjacent ear 122 of the recipient.

As discussed above, speech processing unit 116 generates stimulation data signals that may be used to stimulate the auditory nerve 138. These stimulation signals, however, may have overlapping activation fields, such that certain signals may mask other signals. These masking effects may be estimated using various models such as, for example, the psychoacoustic model, the psycho-electrical model, or an electrophysiological model. These models are discussed in more detail below. In certain embodiments of the present invention, the implant system then takes these estimated masking effects into account when selecting the stimulation signals that will be applied to the auditory nerve 138. The following provides a more detailed description of methods and systems for estimating the masking effects of the stimulations signals and taking these estimated masking effects into account when selecting the stimulation signals that will be applied to auditory nerve 138.

In one embodiment, the implant system uses a psychophysical model, such as for example a psychoacoustic model or a psycho-electrical model. Each of these models provides mathematical models of the masking properties of the human auditory system. A psychoacoustic model takes into account pure tones of different frequencies, while a psycho-electrical model is concerned with electrical stimuli (e.g., pulse bursts) on different electrodes. In an implant system, such as described above, the different electrodes correspond to different frequency bands, and as such, in principal the psycho-electrical model can be translated into the psychoacoustic model. A more detailed description of the psychoacoustic model can be found in Bernd Edler, Heiko Purnhagen, and Charalampos Ferekidis, *ASAC—Analysis/Synthesis Audio Codec for Very Low Bit Rates,* 100th AES Convention, Copenhagen (May 1996); and Frank Baumgarte, Charalampos Ferekidis, and Hendrik Fuchs, *A Nonlinear Psychoacoustic Model Applied to the ISO MPEG Layer 3 Coder,* 99th AES Convention, New York, October 1995 (hereinafter "the Baumgarte reference"), both of which are hereby incorporated by reference herein in their entirety.

Figure 2:
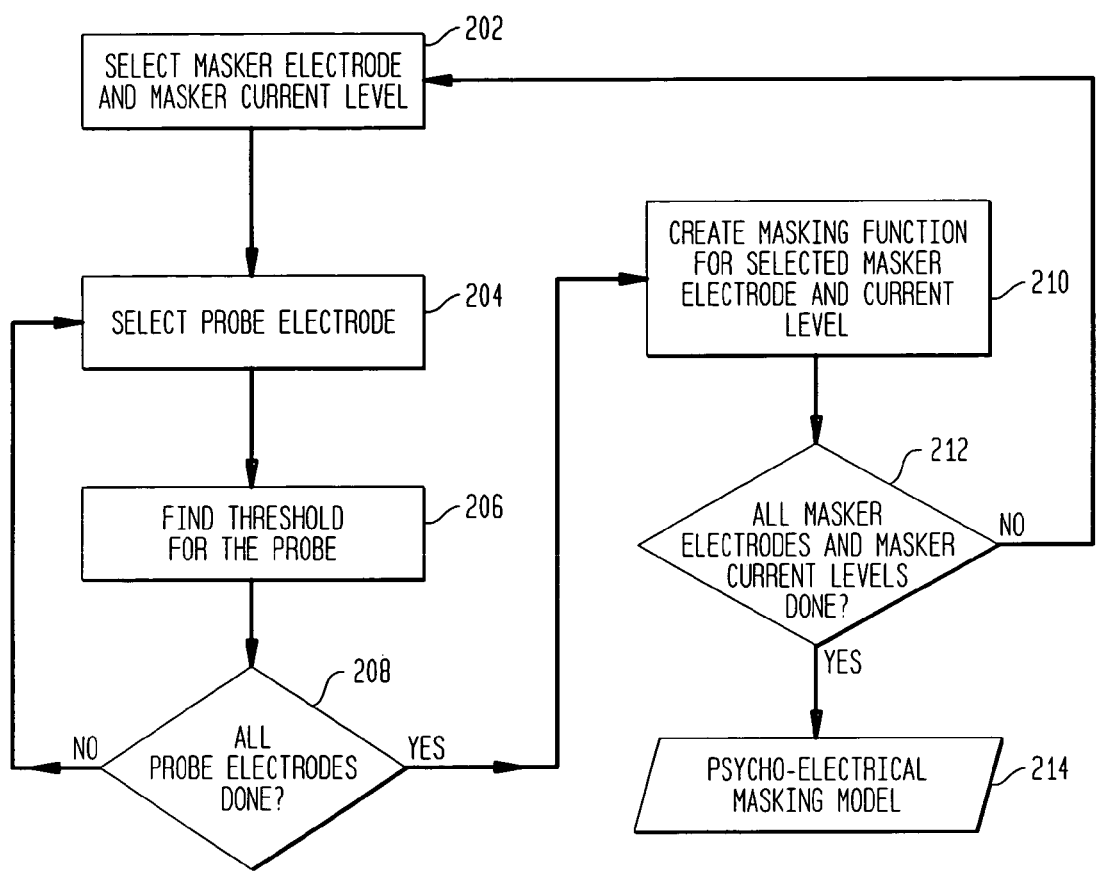
FIG. 2 illustrates a simplified flow chart of an exemplary method for generating a psycho-electrical masking model, in accordance with one embodiment of the present invention.

FIG. 2 illustrates a simplified flow chart of a method for generating a psycho-electrical masking model. FIG. 2 will be described with reference to FIG. 1 where electrode array 134 includes a plurality of electrodes (e.g., 22 electrodes). This flow chart will make references to probes and maskers. A probe is the electrode (or frequency in a psychoacoustic model) for which the amount of masking is being measured and the masker is the electrode (or frequency in a psychoacoustic model) that potentially masks the probe. Initially at block 202, one of the electrodes of electrode array 134 is selected as the masker electrode along with a current level for stimulating the masker electrode. The current for stimulating the masker electrode may be, for example, set as the Maximum Comfort Level (C-level) for the masker electrode, or some value below the C-level but greater than the Threshold current level (T-level) for the masker electrode.

Next, an electrode is selected as the probe electrode at block 204. The threshold for this combination of probe electrode, masker electrode, and masker current level is then determined at block 206. The threshold is the threshold current level for the probe where sound for the probe first becomes audible to the implant recipient in the presence of stimulation by the masker electrode at the masker current level. In psychophysical models, this threshold is also referred to as a detection threshold.

In this example, the threshold may be determined by first stimulating the masker electrode followed by the probe electrode. This technique is referred to as forward masking. In other examples, a backward masking technique may be used where the probe electrode is stimulated before the masker electrode, or, for example, the probe and masker electrodes may be stimulated simultaneously (i.e., simultaneous masking).

In determining the threshold, the probe current level (PCL) may initially be set at a low level and then be gradually increased until the implant recipient can hear the probe sound. The implant recipient may indicate whether or not they can hear any sound from the probe electrode by, for example, pressing down a button if they hear the sound and releasing it if the sound becomes inaudible. A further description of techniques for measurement of psychophysical forward masking is provided in Lawrence T. Cohen, Louise M. Richards, Elaine Saunders, and Robert S. C. Cowen, *Spatial Spread of Neural Excitation in Cochlear Implant Recipients: Comparison of Improved ECAP Method and Psychophysical Forward Masking*, 179 Hearing Res. 72-87 (May 2003) (hereinafter "the Cohen et al. 2003 paper"), which is hereby incorporated by reference herein in its entirety.

After the threshold for this combination of masker and probe electrode is determined, it is next determined at block 208 whether other probe electrodes should also be checked. Preferably the detection threshold for every combination of masker electrode and probe electrode is determined. Thus, if there are more probe electrodes to check for this particular masker electrode, the process returns to block 204 and finds the detection threshold for this combination of masker and probe electrodes.

After the thresholds for the probe electrodes of electrode array 134 are determined, a masking function for this masker electrode and masker current level is determined at block 210. A further description of techniques for determining masking functions is provided in the above-referenced Cohen et al. 2003 reference.

Next, at block 212 it is determined whether measurements for other masker electrodes and masker current levels should be taken. If so, the process returns to block 202. If not, the psycho-electrical masking model is determined at block 214 using the above describe masking functions.

The above-described pyschoelectric measurements result in a set of masking functions for different current levels for all electrodes available in the electrode array. A masking function for a given electrode at a given current level is defined by masking thresholds (in current level) (CL) for all electrodes in electrode array 134. This psycho-electrical model may then be translated to a psycho-acoustical model so that instead of being in terms of CLs, it instead is in terms of dB. Additionally, rather than being in terms of electrodes, the measurements may also be translated so that they are instead in terms of the center frequencies of the frequency bands corresponding to the electrodes in array 134, and visa versa. The resulting masking model may then be used when taking masking effects into account when determining the stimulation signals to be used for stimulating electrode array 134, such as is described in further detail below.

Additionally, in another example, a psychoacoustic model in terms of dB can be translated into a model in terms of current levels. This may be accomplished by, for example, using a loudness growth function, such as, for example, a loudness growth function that is in terms of dB on one axis (the x-axis) and in terms of % CL on the other axis (Y-axis), where 100% CL represents the current level corresponding to the maximum point on the curve (measurement). Additionally, this loudness growth function may, for example, be adapted for the implant recipient, and parameters, such as, for example, its steepness (Q-factor) may be adapted according to feedback from the implant recipient. As one or ordinary skill in the art would appreciate, it is not necessary to translate current level back to dB and electrode back to frequency, or visa versa; in alternative embodiments the values of either the psycho-electrical model or the psychoacoustic model may be used when taking masking effects into account when selecting stimulations signals, as is described in further detail below.

In addition to the above-described psychophysical models, in other embodiments, the implant system may use an electrophysiological model. For example, the above-described method of FIG. 2 may be adapted for determining an electrophysiological model. In such, an example, rather determining a detection threshold using psychophysical measurements in step S206, the method instead determines the masking threshold based on electrophysiological measurements. These measurements may include for example measuring Electrical Compound Action Potentials (ECAP) of the auditory nerve, Electrically Evoked Auditory Brainstem Potentials (EABP) or Cortically Evoked Potentials (CEP). The following provides a more detailed description of exemplary methods for determining an electrophysiological model for use by an implant system.

In one embodiment, the implant system is a Nucleus® 24 cochlear implant system or a Nucleus® Freedom™ cochlear implant system commercially available from Cochlear Limited, Australia, in which electrode array includes a plurality of electrodes (e.g., 22). Further, in this example, implant system 100 includes a version of Cochlear's Neural Response Telemetry (NRT™) software, such as, for example, version 3.0 or the Custom Sound EP™ software. The NRT software and the Custom Sound EP software can be used to record ECAP potentials of the auditory nerve in Nucleus 24 or Nucleus Freedom implant users. To record a ECAP in cochlear implant users the masker and probe electrode are selected as the same electrode. Masker stimulation signals and probe stimulation signals are then applied to the electrode and the response measured by a recording electrode close to the stimulation electrodes. A subtraction method is used to minimize the stimulation artifact. For example, electrophysiological measurements measure nerve tissue potentials. The amplitudes of these potentials are typically in the 1-500 microvolt range and may be evoked by electrical stimuli that create an artifact that may by up to 10000 times larger than the response that is trying to be measured. Thus, a subtraction technique, such as discussed above may be used to minimize this artifact. A complete description of the subtraction method can be found in Abbas P J, Brown C J, Hughes M L, Ganz B J, Wolayer A A, Gervais J P and Hong S H, *Electrically evoked compound action potentials recorded from subjects who use the nucleus CI24M device*, Ann Otol Rhinol Laryngol Suppl. 2000 December; 185:6-9 (hereinafter "the Abbas et al 2000 paper"), which is hereby incorporated by reference herein in its entirety.

A description of masker and probe stimuli and there use in determining spread of excitation (SOE) curves for an implant recipient is provided in the above-referenced Cohen et al. 2003 paper and Lawrence T. Cohen, Elaine Saunders, and Louise M. Richardson, *Spatial Spread of Neural Excitation: Comparison of Compound Action Potential and Forward-Masking Data In Cochlear Implant Recipients*, 43 International Journal of Audiology 346-355 (2004), (hereinafter "the Cohen et al. 2004 paper"), which is hereby incorporated by reference herein in its entirety.

Spread of excitation may be determined by varying the recording electrode. The recording electrode is the electrode used to take the measurements (e.g., ECAP) and may be any of the electrodes of electrode array 134. Additionally, the measured response typically decreases in amplitude as the recording electrode is moved away from the masker/probe electrode.

The subtraction method (described elsewhere herein with reference to the Abbas et al 200 paper) and the "Miller technique" can also be used to create a spread of excitation curves. The "Miller technique is described in Miller C A, Abbas P J, Brown C J, *An Improved Method of Reducing Stimulus Artifact in the Electrically Evoked Whole Nerve Potential*, 21(4) Ear Hear 280-90 (August 2000), which is hereby incorporated by reference herein in its entirety. A further description and comparison of mechanisms for generating SOE curves from ECAP measurements is provided in the above-referenced Cohen et al. 2003 paper and Cohen et al. 2004 paper.

Figure 3:
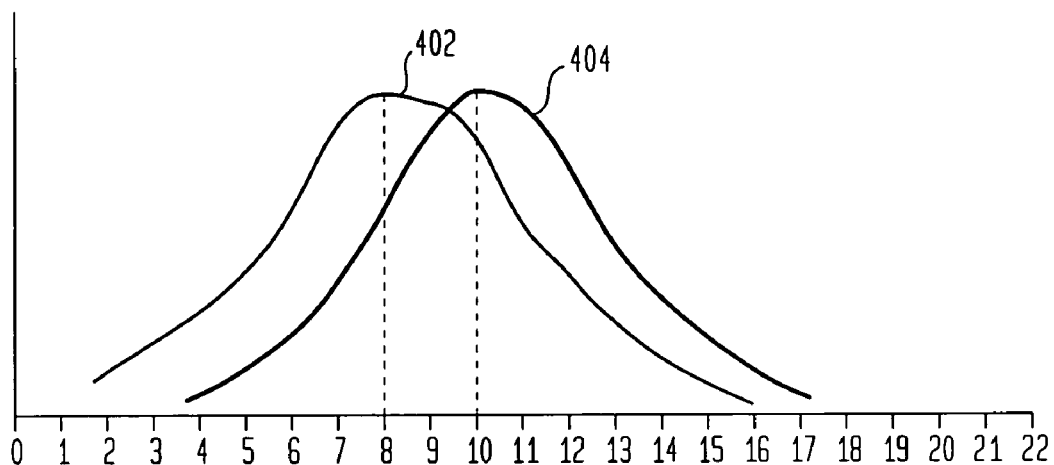
FIG. 3 illustrates a conceptual diagram of overlapping spread of excitations for a marker and a probe, in accordance with one embodiment of the present invention.

Additionally, in another embodiment, the masker and probe electrode need not be the same electrode, but instead may also be different electrodes. In such an example, implant system 100 may include Cochlear's NRT™ software, version 3.0. In this example, when the masker electrode is close to (or the same as) the probe electrode, the masking effect will be at a maximum, and as the masker and probe electrode get further apart the amplitude of the masking will decrease. For example, FIG. 3 illustrates a conceptual diagram of overlapping spread of excitations where the probe electrode is the $8^{th}$ electrode and the masker electrode is the $10^{th}$ electrode of electrode array 134. As illustrated, both the probe excitation field 402 and masker excitation field 404 overlap, thus indicating that there is substantial masking. This overlap may then be measured and used to generate an SOE curve.

Figure 4:
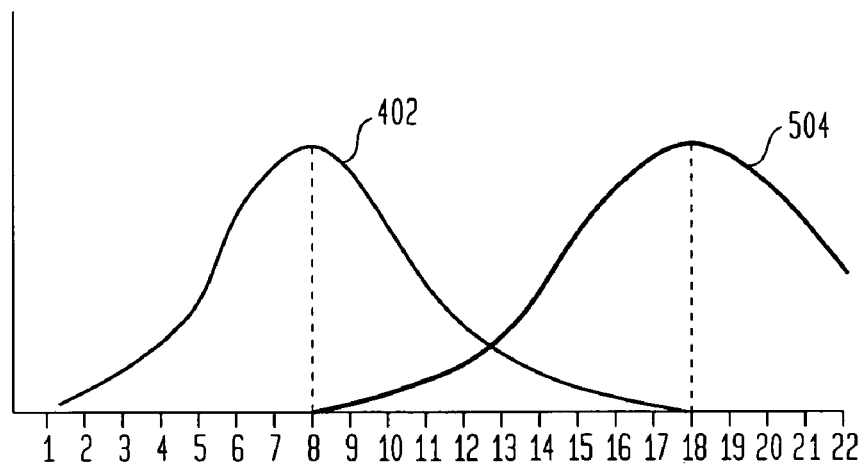
FIG. 4 illustrates a conceptual diagram of overlapping spread of excitations for a marker and a probe, in accordance with one embodiment of the present invention.

FIG. 4 illustrates a conceptual diagram of the overlapping spread of excitations where the probe electrode is still the $8^{th}$ electrode, but the masker electrode has been changed to the $18^{th}$ electrode. As illustrated, the masker's excitation field 504 and the probe's excitation field 402 slightly overlap, thus indicating although there is still some masking, it is less than the amount of masking where the masker electrode was the $10^{th}$ electrode.

An SOE curve measured with the subtraction method for a particular probe electrode may be determined by, for example, taking measurements (e.g., ECAPs) for the probe electrode and every possible masker electrode (i.e., all 22 electrodes of electrode array 134). Then, an SOE curve for a different electrode may be determined by setting it as the probe electrode and taking measurements (e.g., ECAPS) of the amount of masking, again from all possible masker electrodes (e.g., all 22 electrodes). A further description of mechanisms for generating SOE functions where the masker and probe electrodes may be different is provided in the above-referenced Cohen et al. 2003 paper and Cohen et al. 2004 paper. Moreover, rather than taking measurements for every possible masker electrode, in other examples, the masker electrode may be selected to be every other electrode, every fourth electrode, or may vary in any other appropriate way.

In generating the above-discussed SOE curves, various variables may be used, such as, for example, the probe rate, a masker to probe interval (MPI), the number of masking pulses, the rate of the masking pulses, an amplifier gain, the delay of the start of the measurement with respect to the probe pulse, the pulse widths, pulse gaps, or other variables applicable to the NRT™ software. For example, in an embodiment, the MPI interval may be set to +/−400 microseconds and all measurements taken at this MPI. However, in other examples, different MPIs may be used, or, for example, a set of measurements may be taken at one MPI value and then other sets of measurements taken at different MPI values. Further, lower MPI's may be used to mimic high stimulation rates. The number of masker pulses and the masker rate might be varied to mimic temporal effects at different stimulation rates. The probe rate is generally kept at a low rate (±50 Hz) to minimize adaptation effects. Likewise, the other variables may also remain fixed for all measurements, may vary, or different sets of measurements may be taken for different values Additionally, summation effects of masker to probe pulse may be taken into account, such as, for example, when masker to pulse intervals are set to values below 300 microseconds.

Further, in the above examples, the amplitudes of the stimuli for the masker electrode and the probe electrode may be set to be equal. This current level, may be, for example, the Loudest Acceptable Perception Level (LAPL) for the probe electrode, or some value below the LAPL, such, as for example, 80% of the LAPL. Or in other examples, the amplitude for the masker electrode may be set to a value less than the Probe Current Level (PCL) (e.g., 80%, 60%, 40% of the PCL), or even a value greater than the PCL. Further, in other examples, an SOE curve may be determined for one combination of PCL and masker current level, and then other SOE curves determined for different combinations of PCLs and masker current levels. Also, in other examples, information regarding the psychophysical threshold level and the LAPL for each electrode may be taken into account. For example, if the threshold level for a particular electrode that is being used as the masker electrode has a higher threshold level than other electrodes, a corresponding higher masker current level may be used when this particular electrode is the masker electrode.

Additionally, the above discussed measurements (e.g. ECAP) may be taken from the electrode two (2) electrodes above the probe electrode and the electrode two (2) electrodes below the electrode and the measurements are then averaged. These electrodes are referred to the as the recording electrodes. In other examples, different electrodes may be used as the recording electrodes and their results averaged.

Figure 5:
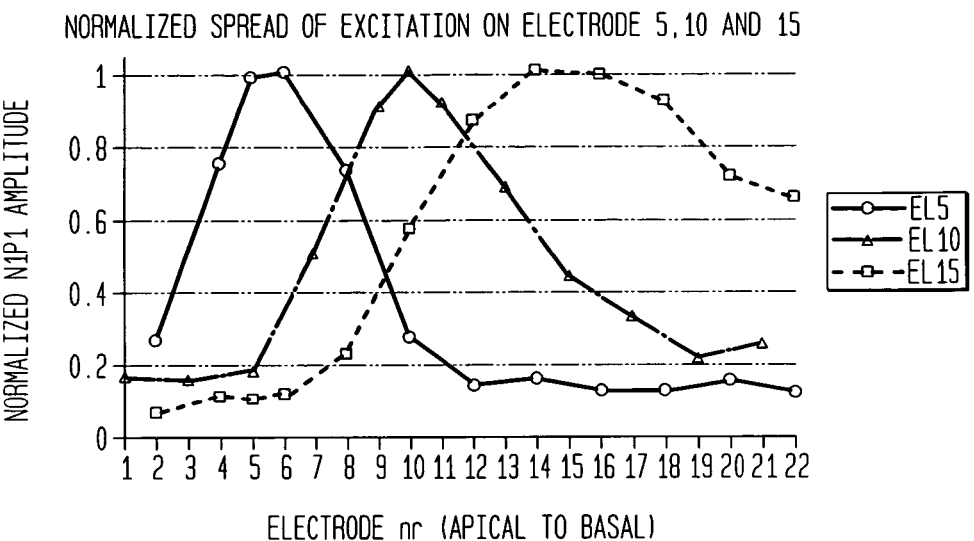
FIG. 5 illustrates exemplary spread of excitation curves for an implant recipient where the Masker and Probe Current Levels were set to be equal, in accordance with one embodiment of the present invention.

FIG. 5 illustrates three exemplary spread of excitation (SOE) curves for an implant recipient where the Masker and Probe Current Levels were set to be equal. In this example, a Masker to Probe Interval of 500 µs was used and the plotted measurements were normalized with respect to the maximum amplitude, which in this example was the determined difference between the first negative peak and first positive peak (N1P1). The first negative occurs where the amplitude first reaches its maximum negative value before the amplitude starts increasing and the first positive occurs where the amplitude reaches it first maximum amplitude before the amplitude starts falling. The exemplary SOE curves illustrated in FIG. 5 depict normalized Spread of Excitation measurements carried out on 3 different electrodes (EL5, EL10 and EL15) in a Nucleus™ Contour Advance recipient. As shown in FIG. 5, the overlap in excitation field may be deduced. For example, EL5 has an excitation field that has overlap with EL2 to EL10, EL10 has an excitation filed that has overlap with EL5 to EL16 and EL15 has overlap with EL8 to 22.

Figure 6:
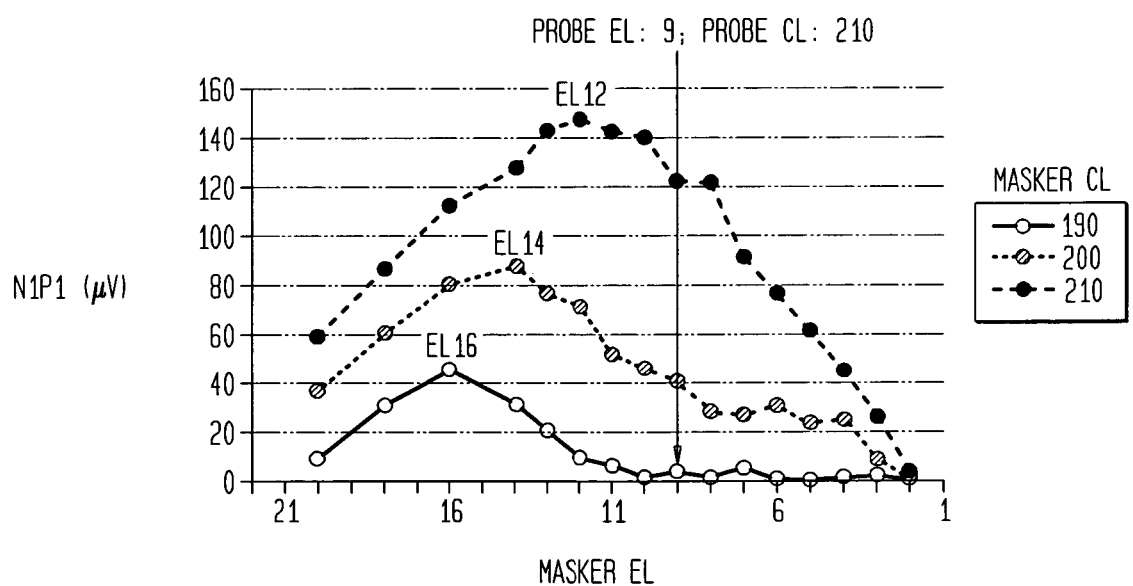
FIG. 6 illustrates another set of exemplary SOE curves for implant recipient, in accordance with one embodiment of the present invention.

FIG. 6 illustrates another set of exemplary SOE curves for implant recipient. In this example, the implant recipient was fitted with a CI24RE cochlear implant, the probe electrode was the set as the $9^{th}$ electrode, and the probe current level was set at 210. Further, in this example, sets of measurements were taken for three different masker current levels (190, 200, and 210). As illustrated, in this example, the SOE is not symmetrical around the probe electrode but is greater towards the apical end of the cochlea (i.e., electrode 12 for MCL=210, electrode 14 for MCL=200, and electrode 16 for MCL=190).

Moreover, if the determined SOE curves have a Y-axis that is in terms of microvolts, in an embodiment, this Y-axis is then translated to current levels (CL) for use when taking masking effects into account when determining the stimulation signals to be used, which is described in further detail below. One exemplary method for translating the Y-axis from microvolts to CL includes determining the dynamic range for each electrode (i.e., the difference between the psychophysical threshold CL and the maximum comfort level CL for the electrode). Then, the masking thresholds in CL may be determined using the following formula:

Masking Threshold on Electrode $X$=Threshold $CL$+ (($SOE$ Amplitude at Electrode $X$)/($SOE$ Maximum Amplitude))*(Dynamic Range of Electrode $X$)

Figure 7:
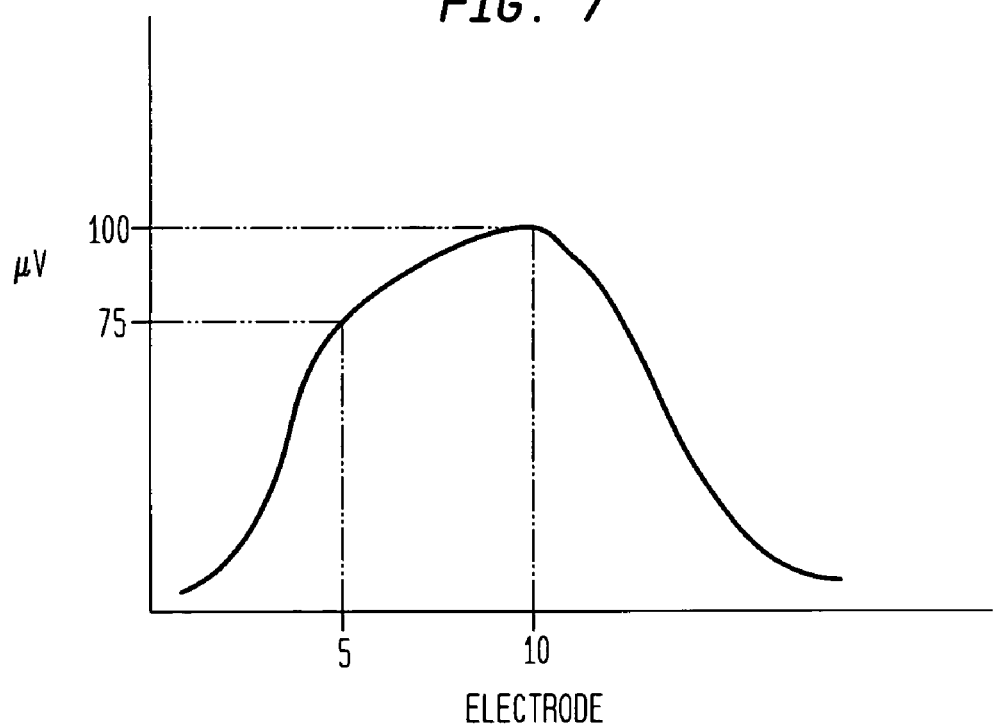
FIG. 7 illustrates an exemplary SOE curve, in accordance with one embodiment of the present invention.

FIG. 7 illustrates an exemplary SOE curve where the masker electrode is electrode 10. Additionally, in this example, electrode 5 has a threshold level of 170 CL and a maximum comfort level of 210 CL (not shown). Thus, the dynamic range for electrode 5 is 40 CL. As shown, the SOE curve has a maximum amplitude of 100 microvolts. Further, the amplitude of the SOE curve at electrode 5 is 75 microvolts. Thus, using the above calculation the masking threshold for electrode 5 is equal to [170+((75)/(100)*40)] or 200 CL. This SOE curve may then be completely translated to CLs by, for example, repeating the above calculation for all electrodes on the X-axis (i.e., all electrodes of electrode array 134). It should be noted that this is but one example of a method for translating an SOE curve from microvolts to CLs, and other methods may be used without departing from the invention.

Further, in one example, once an SOE curve is determined and translated in terms of CLs, it may also be used to generate other SOE curves. Thus, rather than determining SOE curves for all possible combinations of probe electrode and current levels, instead some SOE curves may be interpolated or extrapolated from other SOE curves. For example, an SOE curve determined by measurements, such as those described above, may be used to generate other SOE curves, such as, for example, for different probe current levels. These interpolated SOE curves may be determined by multiplying all values in the original SOE curve by a particular factor. That is, if the maximum current level for the original SOE curve is 200 CL, it may be translated to an SOE curve with a maximum current level of 180 by multiplying all amplitudes by 9/10 (i.e., 180/200). Or in another example, rather than multiplying all amplitudes by a factor, instead a value may be subtracted from all amplitudes. For example, an SOE curve with a maximum amplitude of 200 may be translated to an SOE curve with a maximum amplitude of 180 by subtracting 20 from all the amplitudes.

In addition, to shifting SOE curves in the Y-axis (i.e., by amplitudes), these translated curves may also be shifted in the X-axis (i.e., by electrode). As with Y-axis shifting, this may also be accomplished by multiplying a factor to the X-axis points (i.e., electrodes) or subtracting values from the X-axis points (i.e., electrodes).

Figure 8:
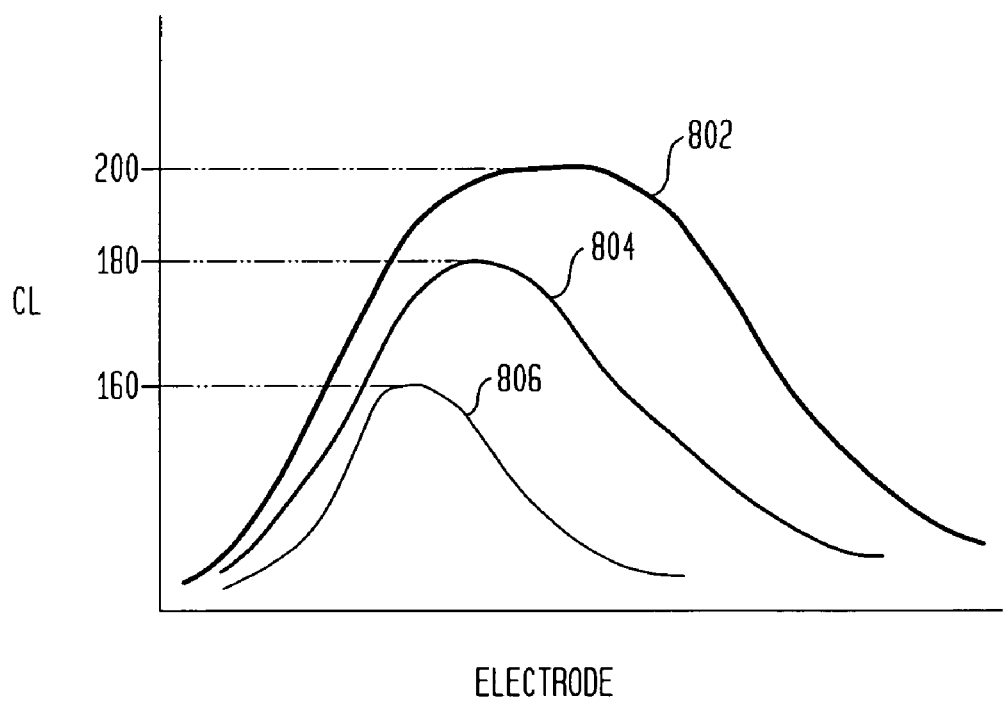
FIG. 8 illustrates a set of exemplary SOE curves exhibiting both Y-axis and X-axis shifting, in accordance with one embodiment of the present invention.

FIG. 8 illustrates a set of exemplary SOE curves exhibiting both Y-axis and X-axis shifting. As illustrated, SOE curve 802 has a maximum current level of 200. This curve may have been determined using a method such as those discussed above. SOE curve 804 may then be generated by translating SOE curve 802 from a maximum current level of 200 to a maximum current level of 180. This may be accomplished by, for example, multiplying the amplitudes of SOE curve 802 by a factor (i.e., 9/10) or by subtracting all amplitudes by a value (i.e., 20). Additionally, the X-axis is also being illustrated as shifting from left to right. This may be accomplished by multiplying or subtracting a value from the X-axis. This value may be based on laboratory measurements indicating an appropriate value for X-axis shifting for this particular implant recipient, or a population of people to which this implant recipient belongs, or the population as a whole. FIG. 8 further illustrates an SOE curve 806 with a maximum current level of 160 that is also generated from translating SOE curve 802 in a like manner. These collections of SOE curves may then be used as the electrophysiological model used for taking masking into account when determining the stimulation signals for stimulating electrode array 134.

FIG. 6 in the Cohen et al 2003 paper shows that psycho-electrically measured forward masking curves and electrophysiological measured SOE curves have a clear overlap. This suggests that the use of both masking models would give similar results when used in a compression algorithm. The advantage of the electrophysiological model is that it can be obtained without subjective feedback from the cochlear implant user. This is particularly important in young children or psychologically disabled cochlear implant users, for whom detection of psychophysical masking would be a too complex task.

Although the above-discussed embodiments for determining an electrophysiological model for a particular implant recipient were discussed with reference to ECAP measurements, in other examples other electrophysiological measurements may be used, such as, for example, EABRs or CEPs.

Figure 9:
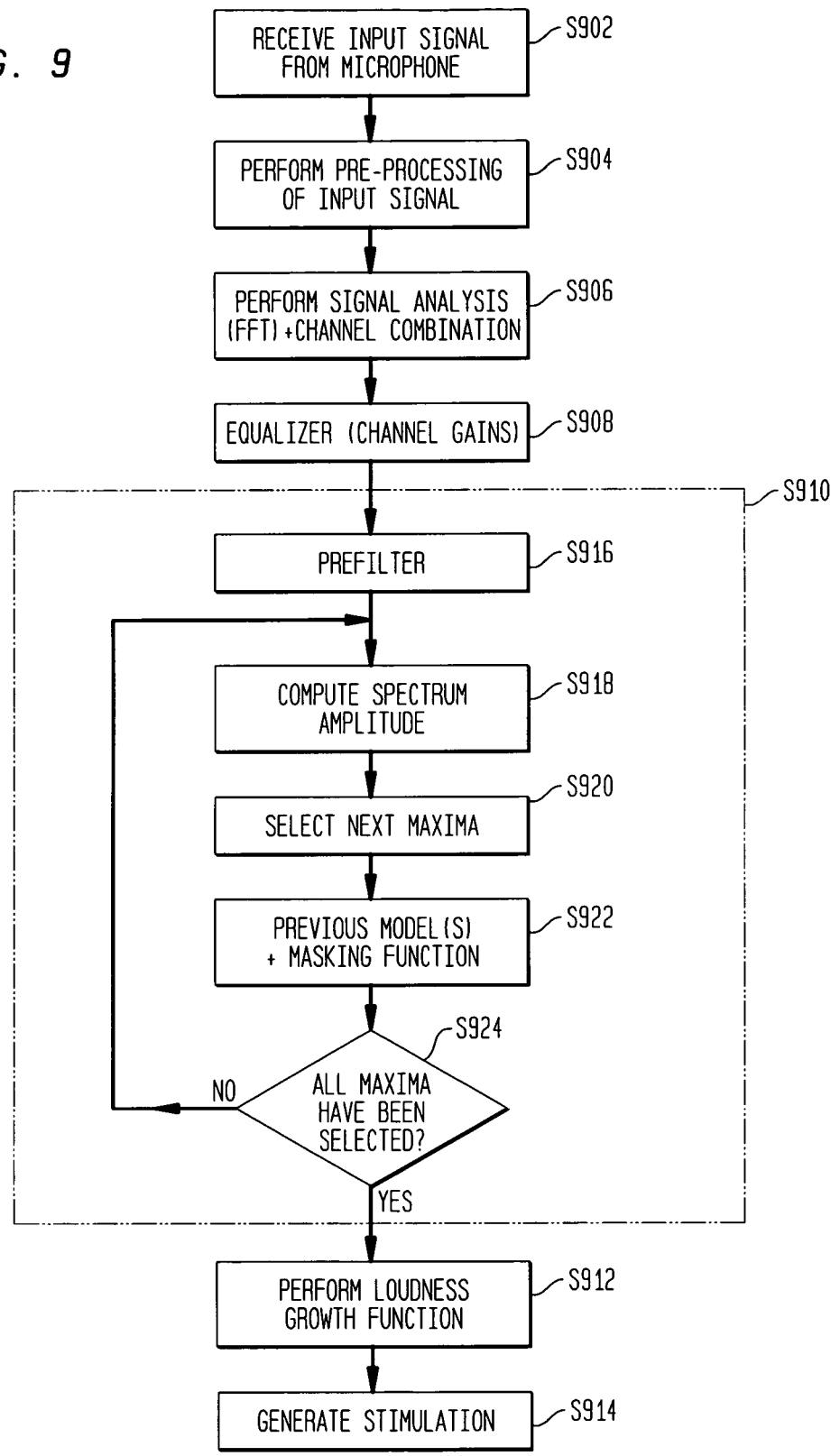
FIG. 9 illustrates an exemplary method for receiving and masking signals, in accordance with one embodiment of the present invention.

FIG. 9 illustrates an exemplary method for receiving and masking signals, in accordance with methods and systems consistent with the invention. At block 902 microphone 120 receives sounds which are converted to electrical signals. These signals may then undergo pre-processing at block 904. This pre-processing may for example, using a pre-emphasis filter, automatic gain control (AGC), and/or manual sensitivity control (MSC), such as for example used in the Advanced Combination Encoder (ACE) strategy.

Figure 10:
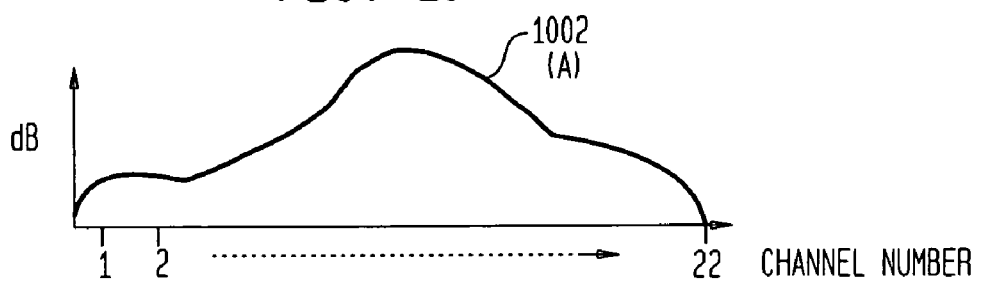
FIG. 10 illustrates an exemplary frequency spectrum of an exemplary received signal, in accordance with one embodiment of the present invention.

These signals next undergo signal analysis at block 906. This may include filtering the signals using a bank of bandpass filters to obtain a plurality of signals as is well-known to those of ordinary skill in the art. Moreover, in an implant system 100 where electrode array 134 includes 22 electrodes, the signal analysis preferably outputs 22 separate output signals, one corresponding to each electrode of electrode array 134. Additionally, in an alternative embodiment, virtual channels may also be generated by, for example, combining the stimulation signals for multiple electrodes, thus resulting in possibly more than 22 output signals. Or, for example, a Fast Fourier Transform (FFT) may be used to generate the frequency spectrum for the received signal. In such an example, the FFT may, for example, compute 22 spectrum amplitudes between 125 and 8 kHz. After signal analysis, the resulting signals may then be equalized at block 908. FIG. 10 illustrates an exemplary frequency spectrum 902 of an exemplary received signal after equalization.

The signal is then compressed and stimulation signals are selected for use by electrode array 134 at block 910. A further description of exemplary methods for compressing the signal are presented below. Next, a loudness growth function may be used on the selected stimulation signals at block 912. After which, the signals may be sent to electrode array 134 for stimulating auditory nerve 138 at block 914.

The following provides a more detailed description of one exemplary method for compressing the signal at block 910. This exemplary method may, for example, be performed by the speech processing unit 116 of implant system 100. Or in other examples, the following method may be performed by other hardware or software, or any combination thereof. Moreover, the following provides one exemplary method, and other methods may be used without departing from the invention.

Figure 11:
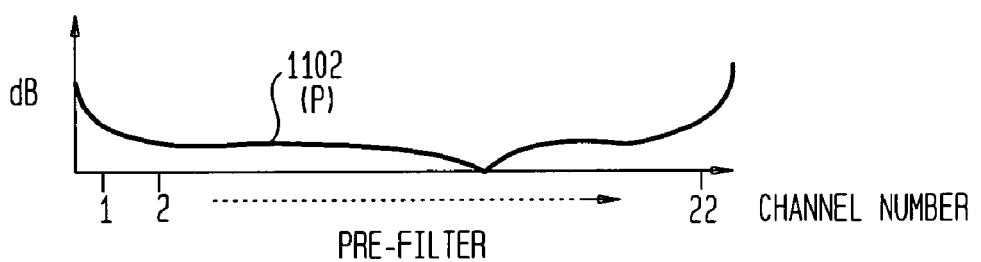
FIG. 11 illustrates an exemplary frequency spectrum of a pre-filter for pre-processing of the signal, in accordance with one embodiment of the present invention.

First, a frequency spectrum for pre-filtering the signal is determined at block 916. FIG. 11 illustrates an exemplary frequency spectrum 1102 of a pre-filter that may be used for pre-processing of the signal. As illustrated, this exemplary pre-filter approximates an equal loudness function. A further explanation of such an exemplary pre-filter is provided in the above-referenced Baumgarte reference.

Figure 12:
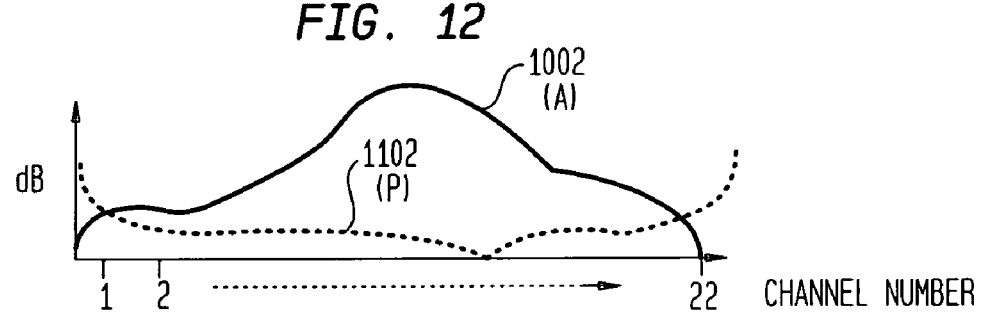
FIG. 12 further illustrates the combination of the frequency spectrum of the exemplary received signal and the frequency spectrum of a pre-filter, in accordance with one embodiment of the present invention.
Figure 13:
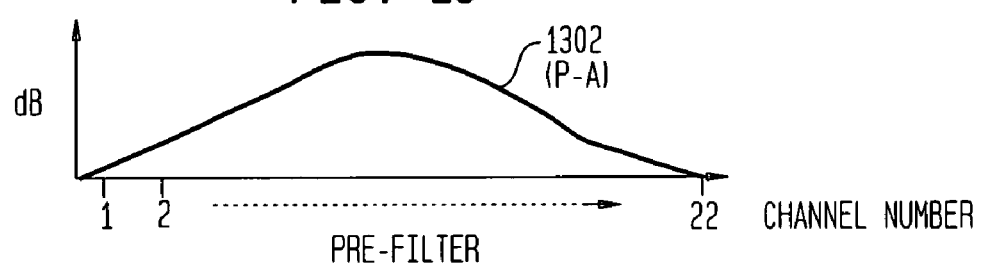
FIG. 13 illustrates a resulting frequency spectrum.
Figure 14:
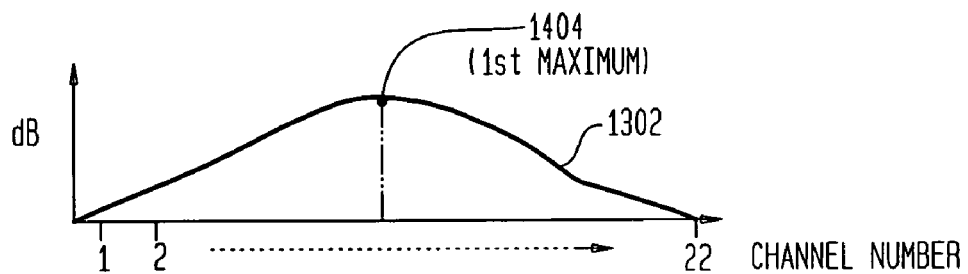
FIG. 14 illustrates a frequency spectrum along with a determined maxima, in accordance with one embodiment of the present invention.

Next, the computed frequency spectrum is applied to the received signal block 918. FIG. 12 further illustrates the combination of the frequency spectrum 1002 of the exemplary received signal and the frequency spectrum 1102 of the pre-filter and FIG. 13 illustrates the resulting frequency spectrum 1302 (i.e. frequency spectrum 1002 minus frequency spectrum 1102). After application of the computed spectrum to the received signal, the maxima (i.e., the channel having the largest amplitude) for the resulting spectrum is determined at block 920. FIG. 14 illustrates resulting frequency spectrum 1302 along with the determined maxima 1404.

After the maxima is determined, the masking effect that would be caused by the selected maxima is determined and this masking effect is combined with the frequency spectrum 1102 of the pre-filter at block 922. The masking effect of the selected maxima is preferably determined using one of the above-discussed models. For example, a psychoacoustic or psycho-electrical model determined for this user may be used. Or, an electrophysiological model may be used. Moreover, rather than using a model generated for this particular implant recipient, in other examples, a model for a particular group of people may be used. For example, if for some reason it is not possible or desirable to measure the masking effect for the implant recipient, the system may instead use a model for a group of people sharing a common characteristic with the implant recipient (e.g., age, sex, etc.). Or, for example, the system may use a generic model for the population as a whole. Additionally, the masking model utilized may be in terms of dB, CL, or microvolts, and as discussed above these models may be translated into one another. In this example, the selected model is translated into a model in terms of CLs and electrodes (if necessary), and this model is used in determining the masking effects for the selected maxima. The combination of the masking effect and the pre-filter will be referred to as the total masking effect.

Figure 15:
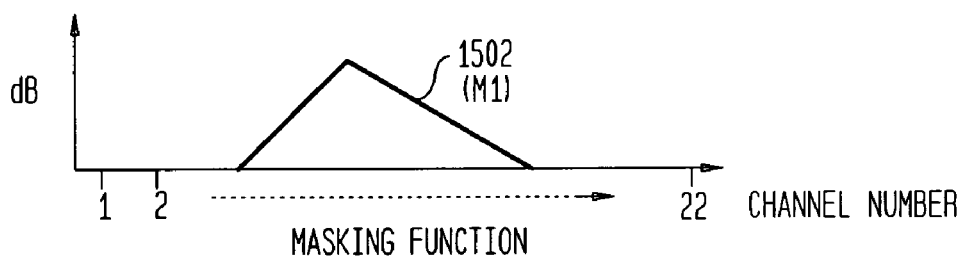
FIG. 15 illustrates an exemplary frequency spectrum of the masking effect for a selected maxima, in accordance with one embodiment of the present invention.
Figure 16:
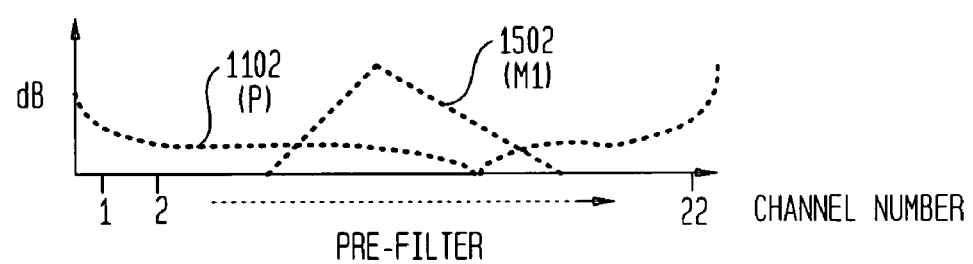
FIG. 16 illustrates an exemplary frequency spectrum of the masking effect for a selected maxima along with the frequency spectrum of a pre-filter, in accordance with one embodiment of the present invention.
Figure 17:
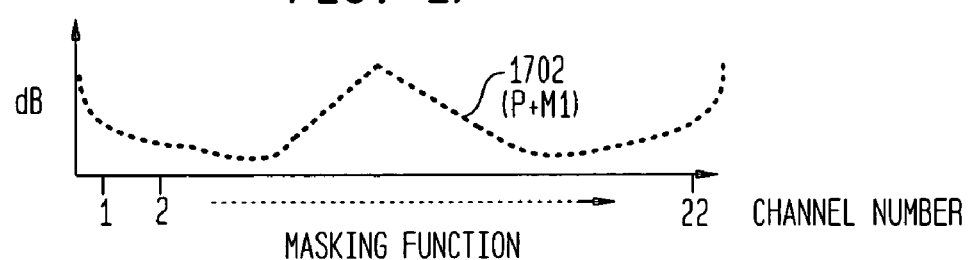
FIG. 17 illustrates a resulting total masking effect, in accordance with one embodiment of the present invention.

FIG. 15 illustrates the exemplary frequency spectrum 1502 of the masking effect for the selected maxima 1404. FIG. 16 illustrates the exemplary frequency spectrum 1502 of the masking effect for the selected maxima 1404 along with the frequency spectrum 1102 of the pre-filter. FIG. 17 illustrates the resulting total masking effect 1702 (i.e. frequency spectrum 1502 plus frequency spectrum 1102).

Next, it is determined whether all desired maxima have been determined at block 924. For example, in one embodiment it may be desirable to determine 8 maxima for stimulation of electrode array 134. Thus, in this example, the process will continue until all 8 maxima are determined or until the total masking effect indicates that no other maxima can be determined (e.g., the combined frequency spectrum of the masking effects is higher at all frequencies than the frequency spectrum of the received signal).

Figure 18:
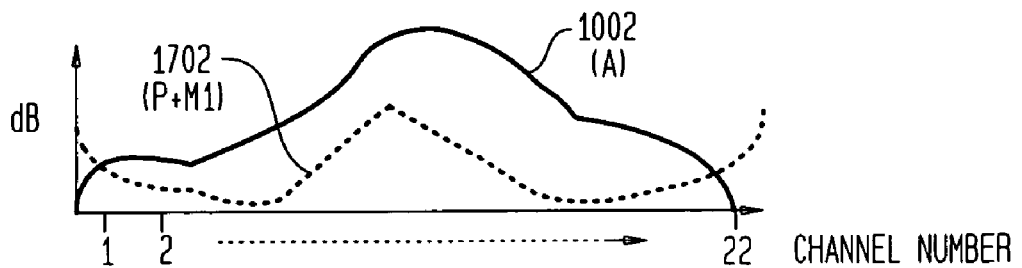
FIG. 18 illustrates the exemplary frequency spectrum of a total masking effect and the frequency spectrum of a received signal, in accordance with one embodiment of the present invention.
Figure 19:
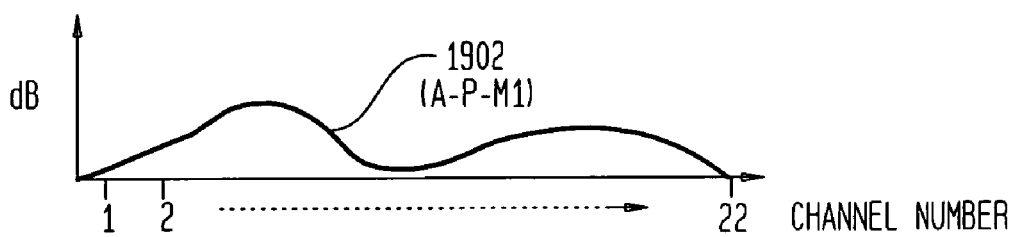
FIG. 19 illustrates a resulting frequency spectrum, in accordance with one embodiment of the present invention.
Figure 20:
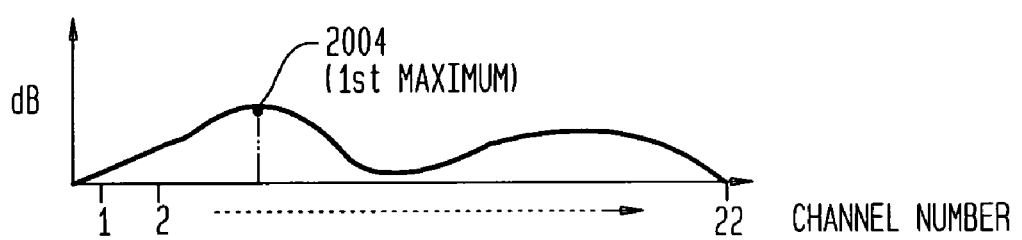
FIG. 20 illustrates a frequency spectrum along with a determined maxima, in accordance with one embodiment of the present invention.

If more maxima should be determined, the process returns to block 918 and the total masking effect is subtracted from the received signal at block 922. FIG. 18 illustrates both the exemplary frequency spectrum 1702 of the total masking effect and the frequency spectrum 1002 of the received signal. FIG. 19 illustrates the resulting frequency spectrum 1902 (i.e. frequency spectrum 1002 minus frequency spectrum 1702). The next maxima is then determined at block 920. FIG. 20 illustrates frequency spectrum 1902 along with determined maxima 2004. Next, the masking effect of this next maxima is determined and is combined with the masking effects of the prior selected maxima and the prefilter at block 922.

If more maxima should be determined at block 924, the process again returns to block 918 and the combined total masking effect is then subtracted from the frequency spectrum 1002 of the received signal and another maxima determined. This process may then repeat until all desired maxima are determined.

Figure 21:
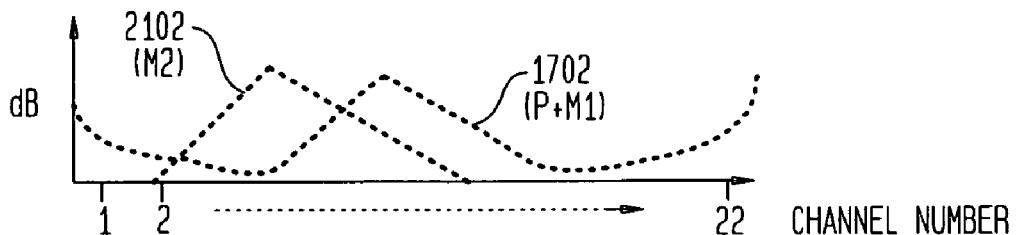
FIG. 21 illustrates a frequency spectrum of a new masker along with a prior determined total masking effect, in accordance with one embodiment of the present invention.
Figure 22:
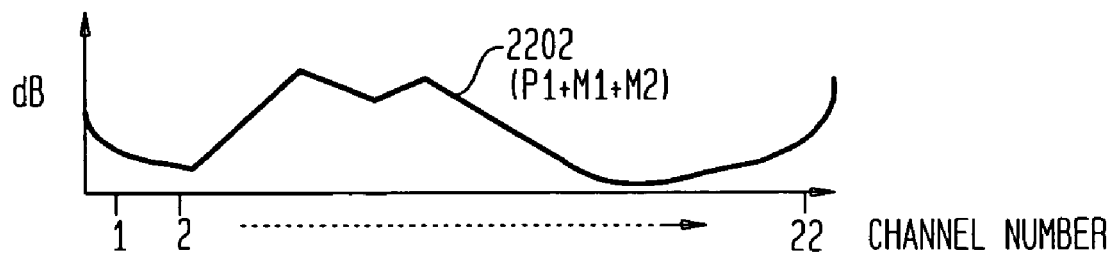
FIG. 22 illustrates a total masking effect frequency spectrum, in accordance with one embodiment of the present invention.
Figure 23:
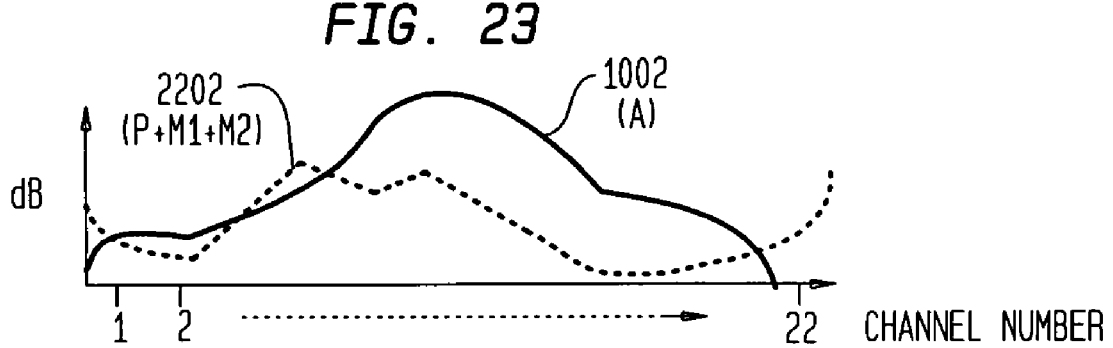
FIG. 23 illustrates a total masking effect frequency spectrum 2102 and a frequency spectrum of a received signal, in accordance with one embodiment of the present invention.
Figure 24:
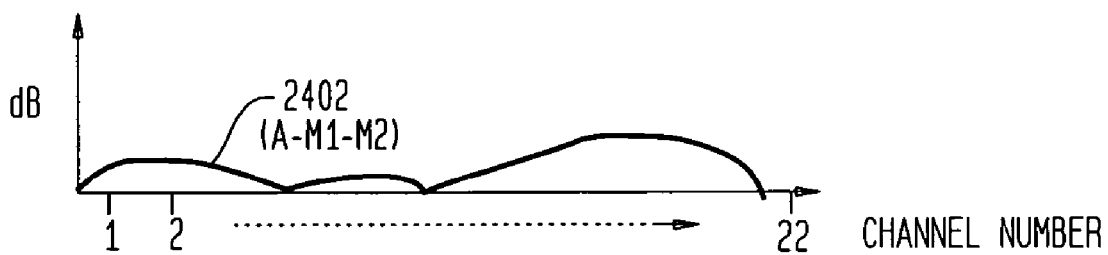
FIG. 24 illustrates a resulting frequency spectrum, in accordance with one embodiment of the present invention.

For example, FIG. 21 illustrates the frequency spectrum 2102 of this new masker along with the prior determined total masking effect 1702. These combine to create the total masking effect frequency spectrum 2202 illustrated in FIG. 22. This total masking effect spectrum 2202 is then subtracted from the frequency spectrum of the received signal 1002 as illustrated in FIG. 23. This results in frequency spectrum 2402 illustrated in FIG. 24. The maxima for this resulting spectrum may then be determined and the process repeated, for example, until all maxima are determined or no other maxima can be determined.

The above described method illustrated in FIG. 9 provides one example of a method for taking masking effects into account when determining stimulation signals for use in an implant system. Other methods of course can be used without departing from the invention. Moreover, as would be apparent to one of skill in the art, the above described steps may be interchanged, combined, or replaced with other steps without departing from the invention, which is defined in the below claims.

In another embodiment, after the measurements for the implant recipients are taken, they are used to create a masking table for the implant recipient. Or, in other examples, a generic masking table may be used that applies, for example, to the population as a whole or to a particular subset of the population to which the implant recipient shares a common characteristic. Additionally, this masking table may be based on psychophysical and/or electrophysiological measurements.

The masking table may, for example, include a set of minimum unmasked levels for each electrode of electrode array 134. This minimum unmasked level is the minimum current level above which the signal will not be masked. An exemplary masking table is listed below.

As shown, the masking table may include a column identifying each electrode of electrode array 134 along with corresponding minimum unmasked levels. Each unmasked level may, for example, give the minimum stimulus level (e.g., minimum current level) to electrode n which will elicit a response immediately following a stimulus to one or more relevant electrodes. In a complete masking model all electrodes of the array could be considered as relevant. Further, these minimum levels may be expressed as values between the psychophysical threshold (T) and psychophysical maximum comfort (C) levels of the corresponding electrode. The threshold (T) and maximum comfort (C) levels may be determined during the fitting of implant system 100.

| MINIMUM UNMASKED LEVELS | |
|---|---|
| Electrode | Minimum Unmasked Levels |
| 1 | $M_{1,T}, M_{1,T+1}, \ldots M_{1,C-1}, M_{1,C}$ |
| 2 | $M_{2,T}, M_{2,T+1}, \ldots M_{2,C-1}, M_{2,C}$ |
| . | . |
| . | . |
| . | . |
| n − 1 | $M_{n-1,T}, M_{n-1,T+1}, \ldots M_{n-1,C-1}, M_{n-1,C}$ |
| N | $M_{n,T}, M_{n,T+1}, \ldots M_{n,C-1}, M_{n,C}$ |
| n + 1 | $M_{n+1,T}, M_{n+1,T+1}, \ldots M_{n+1,C-1}, M_{n+1,C}$ |
| . | . |
| . | . |
| . | . |
| . | . |
| . | . |

It should be understood this is but one example of a masking table and other types of masking tables may be used without departing from the invention. This determined table may then be used in implementing a masking scheme to delete or replace signals.

Figure 25:
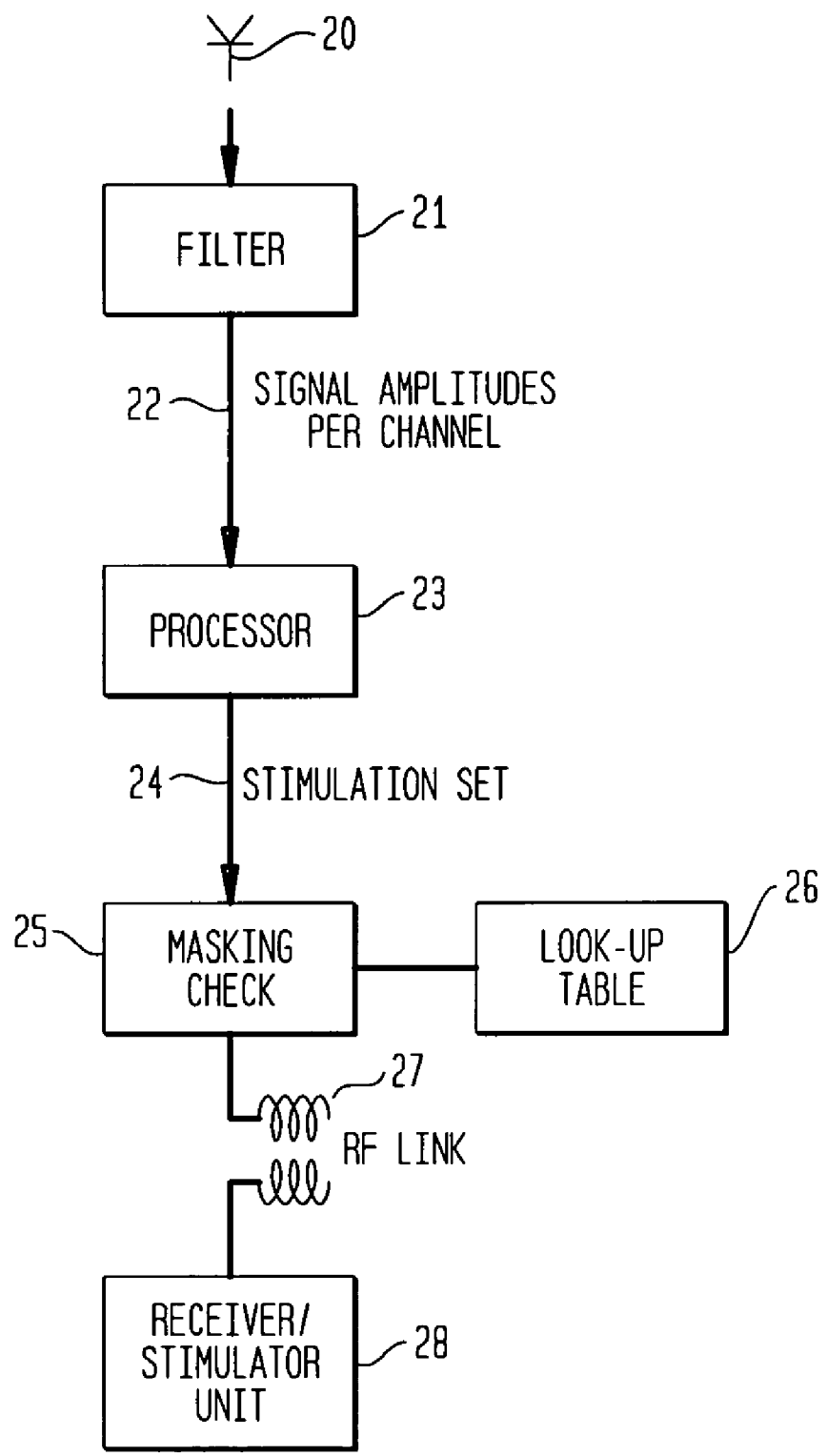
FIG. 25 illustrates an exemplary flow chart of a method for checking of masked signals, in accordance with one embodiment of the present invention.

FIG. 25 illustrates an exemplary flow chart of a method for masking signals. As illustrated, sound signals are detected by microphone 20. These signals are then processed into a predetermined number of frequency channels by filter 21. The output of filter 21 is a set of signal amplitudes per channel 22. Processor 23, in simple terms, selects certain channels as the basis for stimulation, based on amplitude or other factors. A set of stimulation instructions for implanted receiver stimulator unit 28 is thereby produced. These instructions include at least the electrode or electrodes to be stimulated, and the amplitude of the stimulus to be applied. These steps may also include, for example, the processing and equalization discussed above with reference to FIG. 9. Moreover, these steps may occur in speech processing unit 116 or, for example, in other hardware or software or any combination thereof.

After the stimulation signals are generated and processed, they may next undergo a Making Check 25. Masking Check 25 involves comparing each successive two or more stimuli with the look-up table to determine whether they match a predetermined masking rule in look-up table 26. Further, the masking table 26 and masking check 25 may be stored and performed by speech processing unit 116, or by, for example, other hardware or software, or any combination thereof.

The masking check output is thus the stimulation set, with masked stimuli excluded. This is then transmitted conventionally, for example via an RF link 27 to the implanted receiver/stimulator unit 28, which operates conventionally.

Although the above described embodiments were discussed with reference to a cochlear implant, in other embodiments these methods and systems may be used with other implant systems such as, for example, in an auditory brainstem implant or an electroacoustical device for a user.

All documents, patents, journal articles and other materials cited in the present application are hereby incorporated by reference.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of neural stimulation, comprising:
   determining a plurality of stimulation signals based on a received acoustical signal;
   selecting a subset of one or more of the plurality of stimulation signals based on information indicative of a masking effect of at least one of the plurality of stimulation signals; and
   applying stimuli to a user representative of the received acoustical signal using only the selected subset of stimulation signals.

2. The method of claim 1, wherein the information indicative of the masking effect is derived from a model indicative of a masking effect for a population of people.

3. The method of claim 2, wherein the plurality of people is a subset of people sharing a common characteristic.

4. The method of claim 1, wherein the information indicative of the masking effect is derived from a user-specific model determined for the recipient.

5. The method of claim 1, wherein the information indicative of the masking effect is derived from psychophysical measurements.

6. The method of claim 5, wherein the psychophysical measurements are psychoacoustic measurements.

7. The method of claim 5, wherein the psychophysical measurements are psycho-electrical measurements.

8. The method of claim 1, wherein the information indicative of the masking effect is determined by applying a masker stimulus on a masker electrode of an electrode array implanted in the user and determining a threshold value for a probe stimulus on a probe electrode above which sound from the probe stimulus is audible to the user in the presence of the masker stimulus.

9. The method of claim 1, wherein the information indicative of a masking effect is derived from electrophysiological measurements.

10. The method of claim 9, wherein the electrophysiological measurements are determined by measuring Electrically Evoked Compound Action Potentials.

11. The method of claim 9, wherein the electrophysiological measurements are determined by measuring Electrically Evoked Auditory Brainstem Potentials.

12. The method of claim 9, wherein the electrophysiological measurements are determined by measuring Conically Evoked potentials.

13. The method of claim 1, further comprising:
   applying a masker signal on a first electrode of an electrode array implanted in the recipient; and
   applying a probe signal on a second electrode of the electrode array; and:

measuring a threshold indicative of neural activity of the recipient due to the application of the masker and probe signals.

14. The method of claim 1, wherein selecting a subset of one or more of the stimulation signals, comprises:
   selecting a subset of stimulation signals from the determined plurality of stimulation signals based on an amplitude for each of the plurality of stimulation signals;
   determining whether one or more of the selected subset of stimulation signals is masked by other signals in the selected subset of stimulation signals based on information indicative of a masking effect of one or more of the other stimulation signals;
   modifying the selected subset of stimulation signals based on the determination of whether one or more of the selected subset of stimulation signals is masked.

15. The method of claim 14, wherein modifying the selected plurality of stimulation signals comprises:
   deleting stimulation signals from the subset that were determined to be masked.

16. The method of claim 1, wherein selecting a subset of one or more of the stimulation signals comprises:
   selecting a first stimulation signal from the determined plurality of stimulation signals based on an amplitude of the first stimulation signal;
   determining a masking effect of the selected stimulation signal; and
   selecting a next stimulation signal from the determined plurality of stimulation signals based on an amplitude of the next stimulation signal and the determined masking effect.

17. The method of claim 16 further comprising:
   iteratively performing the steps of determining a masking effect of the selected stimulation signals and selecting a next stimulation signal until a predetermined number of stimulation signals are selected.

18. The method of claim 1, wherein the applying the stimuli to the user comprises:
   electrically stimulating the auditory system.

19. The method of claim 1, wherein applying the stimuli to the user comprises:
   applying the stimuli using an electrode array comprising a plurality of electrodes.

20. The method of claim 1, wherein the user has a cochlear implant and wherein applying the stimuli to the user comprises:
   applying the stimuli using the cochlear implant.

21. The method of claim 1, wherein the user has an auditory brainstem implant and wherein applying the stimuli to the user comprises:
   applying the stimuli using the auditory brainstem implant.

22. The method of claim 1, wherein the user uses an electroacoustical device, and wherein applying the stimuli to the user comprises:
   applying the stimuli using the electroacoustical device.

23. The method of claim 1, wherein the information indicative of a masking effect takes temporal masking effects into account.

24. A system for neural stimulation, comprising:
   a microphone configured to receive an acoustical signal;
   a speech processing unit configured to generate a plurality of stimulation signals based on the received acoustical signal and to select a subset of one or more of the plurality of stimulation signals based on information indicative of a masking effect of at least one of the plurality of stimulation signals; and
   an implant configured to apply stimuli to a user representative of the received acoustic signal using only the selected subset of stimulation signals.

25. The system of claim 24, wherein the information indicative of the masking effect is derived from a model indicative of a masking effect for a population of people.

26. The system of claim 25, wherein the plurality of people is a subset of people sharing a common characteristic.

27. The system of claim 24, wherein the information indicative of the masking effect is derived from a user-specific model determined for the recipient.

28. The system of claim 24, wherein the information indicative of the masking effect is derived from psychophysical measurements.

29. The system of claim 28, wherein the psychophysical measurements are psychoacoustic measurements.

30. The system of claim 28, wherein the psychophysical measurements are psycho-electrical measurements.

31. The system of claim 24, wherein the information indicative of the masking effect is determined by applying a masker stimulus on a masker electrode of an electrode array implanted in the user and determining a threshold value for a probe stimulus on a probe electrode above which sound from the probe stimulus is audible to the user in the presence of the masker stimulus.

32. The system of claim 24, wherein the information indicative of a masking effect is derived from electrophysiological measurements.

33. The system of claim 32, wherein the electrophysiological measurements are determined by measuring Electrically Evoked Compound Action Potentials.

34. The system of claim 32, wherein the electrophysiological measurements are determined by measuring Electrically Evoked Auditory Brainstem Potentials.

35. The system of claim 32, wherein the electrophysiological measurements are determined by measuring Cortically Evoked potentials.

36. The system of claim 24, wherein the speech processing unit, in selecting a subset of one or more of the stimulation signals, is further configured to select a subset of stimulation signals from the determined plurality of stimulation signals based on an amplitude for each of the plurality of stimulation signals; determine whether one or more of the selected subset of stimulation signals is masked by other signals in the selected subset of stimulation signals based on information indicative of a masking effect of one or more of the other stimulation signals; and modify the selected subset of stimulation signals based on the determination of whether one or more of the selected subset of stimulation signals is masked.

37. The system of claim 36, wherein the speech processing unit, in modifying the selected plurality of stimulation signals signals, is configured to delete stimulation signals from the subset that were determined to be masked.

38. The system of claim 24, wherein the speech processing unit, in selecting a subset of one or more of the stimulation signals, is further configured to select a first stimulation signal from the determined plurality of stimulation signals based on an amplitude of the first stimulation signal; determine a masking effect of the selected stimulation signal; and select a next stimulation signal from the determined plurality of stimulation signals based on an amplitude of the next stimulation signal and the determined masking effect.

39. The system of claim 38 wherein the speech processing unit is configured to iteratively perform the steps of determining a masking effect of the selected stimulation signals and selecting a next stimulation signal until a predetermined number of stimulation signals are selected.

40. The system of claim 24 wherein the implant is configured to electrically stimulate the auditory system.

41. The system of claim 24, wherein the comprises an electrode array having a plurality of electrodes.

42. The system of claim 24, wherein the implant is a cochlear implant.

43. The system of claim 24, wherein the implant is an auditory brainstem implant.

44. The system of claim 24, wherein the implant is an electroacoustical device.

45. The system of claim 24, wherein the information indicative of a masking effect takes temporal masking effects into account.

46. A system for neural stimulation, comprising:

means for determining a plurality of stimulation signals based on a received acoustical signal;

means for selecting a subset of one or more of the plurality of stimulation signals based on information indicative of a masking effect of at least one of the plurality of stimulation signals; and means for applying stimuli to a user representative of the received acoustical signal using only the selected subset of stimulation signals.

* * * * *